(12) United States Patent
Sooryakumar et al.

(10) Patent No.: US 8,906,691 B2
(45) Date of Patent: Dec. 9, 2014

(54) MAGNETIC PLATFORMS FOR BIOMOLECULE TRAPPINGS, MANIPULATIONS, AND SORTING

(71) Applicants: Ratnasingham Sooryakumar, Columbus, OH (US); Thomas Charles Henighan, Columbus, OH (US); Gregory B. Vieira, Columbus, OH (US); Jeffrey J. Chalmers, Columbus, OH (US)

(72) Inventors: Ratnasingham Sooryakumar, Columbus, OH (US); Thomas Charles Henighan, Columbus, OH (US); Gregory B. Vieira, Columbus, OH (US); Jeffrey J. Chalmers, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 14/211,731

(22) Filed: Mar. 14, 2014

(65) Prior Publication Data

US 2014/0199747 A1 Jul. 17, 2014

Related U.S. Application Data

(62) Division of application No. 13/147,689, filed as application No. PCT/US2010/023472 on Feb. 8, 2010, now Pat. No. 8,691,557.

(60) Provisional application No. 61/150,363, filed on Feb. 6, 2009.

(51) Int. Cl.
*G01N 33/68* (2006.01)
*G01N 33/569* (2006.01)
*C12N 13/00* (2006.01)
*G01N 33/543* (2006.01)

(52) U.S. Cl.
CPC ............ *C12N 13/00* (2013.01); *G01N 33/6854* (2013.01); *G01N 33/56966* (2013.01); *G01N 33/54326* (2013.01); *G01N 33/54366* (2013.01)
USPC .......................................................... 436/43

(58) Field of Classification Search
CPC ..................................................... C12M 1/266
USPC .......................................................... 436/43
See application file for complete search history.

(56) References Cited

FOREIGN PATENT DOCUMENTS

WO 2009143444 A1 11/2009

*Primary Examiner* — Sally Merkling
(74) *Attorney, Agent, or Firm* — Dinsmore & Shohl LLP

(57) ABSTRACT

A magnetic platform is provided and includes a patterned array of discrete magnetic elements positioned on a substrate, a plurality of first electromagnets for creating a first magnetic field substantially in the plane of the substrate, an electromagnetic coil for creating a second magnetic field substantially perpendicular to the plane of the substrate, and a control device for controlling the application of the magnetic fields. Processes for manipulating, transporting, separating and sorting micro- or nano-scale particles and biomolecules are also described.

12 Claims, 8 Drawing Sheets

MAGNETIC PLATFORMS FOR BIOMOLECULE TRAPPINGS, MANIPULATIONS, AND SORTING

CROSS-REFERENCE TO RELATED APPLICATIONS

This application is a divisional of U.S. application Ser. No. 13/147,689 filed Aug. 3, 2011, which is based on U.S. national phase entry of International Application No. PCT/US2010/023472 filed Feb. 8, 2010, which claims the benefit of U.S. Provisional Application Ser. No. 61/150,363 filed Feb. 6, 2009.

BACKGROUND

This disclosure relates to magnetic array platforms that provide trapping, manipulation, and transport of individual micro- or nano-scale particles such as cells, viruses, DNA, proteins, and other biomolecules.

Historically, sorting technologies have focused on gross physical characteristics, such as particle size or density, or utilized some affinity interaction, such as receptor-ligand interactions or reactions with immunologic targets.

Electromagnetic response properties have also been utilized for particle sorting and characterization. For example, dielectrophoretic separators utilize non-uniform DC or AC electric fields for separation of particles. See, e.g., U.S. Pat. No. 5,814,200, Pethig et al., entitled "Apparatus for Separating By Dielectrophoresis."

Coherent light has been used to trap and manipulate particles. One of the earliest workers in the field was Ashkin, U.S. Pat. No. 3,808,550 entitled "Apparatuses for Trapping and Accelerating Neutral Particles" which disclosed systems for trapping and containing particles through radiation pressure. Lasers generating coherent optical radiation were the preferred source of optical pressure.

Other particle manipulation techniques include the use of atomic force microscopy (AFM) or magnetic force microscopy (MFM). An AFM uses a cantilever, sometimes with a receptor attached to the cantilever tip, to identify and manipulate a single cell or protein on a surface by stretching the cell in an out-of-plane direction. Similarly, an MFM utilizes a magnetic field to manipulate and stretch a cell or protein with a magnetic bead attached thereto in an out-of-plane direction.

The sorting of individual cells or micro- or nano-scale particles is an old problem, whether attempting to isolate a single cell or particle, or identifying a specific sub-population of cells or particles that behave differently or have different properties than the rest of the population. While instruments and techniques exist to enable cells or particles to be seen, manipulation of single cells or particles, or groups of them within a larger population, has been problematic.

As noted above, one traditional method of cell manipulation involves laser capture in which cells can be trapped using a laser beam. However, such systems are slow, laser power intensive, and the process cannot be automated to isolate and manipulate large cell populations. Another traditional method, atomic force microscopy, can be used to identify and manipulate a single cell. However, it cannot be used to isolate and manipulate a population of cells.

Accordingly, the need still exists for a technique which can isolate, sort, and manipulate individual biomolecules, including cells, proteins, and peptides and then can readily manipulate the biomolecules for testing, or to separate them from a heterogeneous population. Desirably, such a technique would be able to manipulate thousands or tens of thousands of biomolecules within a short period of time.

SUMMARY

The present disclosure relates to magnetic array platforms that provide trapping, manipulation, and transport of individual micro- or nano-scale particles such as cells, viruses, DNA, proteins, and other biomolecules. The term "biomolecules" as used herein encompasses all of these micro- or nano-scale particles including, but not limited to, cells, viruses, DNA, proteins, and peptides. Although the processes of the present disclosure are not limited to particular platforms or the context in which they are used, for the purposes of illustration, the process steps are illustrated herein with reference to specific magnetic platforms.

In accordance with one embodiment of the present disclosure, a magnetic platform is provided and includes a patterned array of discrete magnetic elements positioned on a substrate, a plurality of first electromagnets positioned adjacent to the substrate for creating a first magnetic field substantially in the plane of the substrate, and an electromagnetic coil positioned adjacent to the substrate for creating a second magnetic field substantially perpendicular to the plane of the substrate. The magnetic platform may also comprise a control device for controlling the application of the first and second magnetic fields.

In accordance with another embodiment, a process for manipulating a biomolecule in substantially one plane that includes providing a patterned array of discrete magnetic elements positioned on a substrate and a biomolecule having magnetic particles attached thereto. The biomolecule is trapped on the patterned array, and then manipulated by controlling the magnetic field.

In accordance with another embodiment of the present disclosure, a process for sorting biomolecules is provided and includes providing a suspension of mixed biomolecules and a magnetic platform including a patterned array of discrete magnetic elements positioned on a substrate, a plurality of first electromagnets positioned adjacent to the substrate for creating a first magnetic field substantially in the plane of the substrate, an electromagnetic coil positioned adjacent to the substrate for creating a second magnetic field substantially perpendicular to the plane of the substrate, and a control device for controlling the application of the first and second magnetic fields. Antibody-magnetic particle conjugates for a first biomolecule type are added to the suspension to couple with a first biomolecule type, and the magnetic fields are selectively controlled to cause the coupled first biomolecule type to be sorted from the cell suspension.

In accordance with another embodiment of the present disclosure, a process for separating biomolecules is provided and includes a magnetic platform that includes a patterned array of discrete magnetic elements positioned on a substrate, a plurality of first electromagnets for creating a first magnetic field, an electromagnetic coil for creating a second magnetic field and a control device for controlling the application of the first and second magnetic fields. A mixture of magnetically labeled and unlabeled biomolecules is flowed through a first fluid channel, trapping the magnetically labeled biomolecules on the magnetic platform. The magnetic fields produced by the platform to cause the magnetically labeled biomolecules to be transported from the first fluid channel to a second fluid channel. The magnetically labeled biomolecules are then detached from the platform in the second fluid channel.

The following detailed description of specific embodiments of the present disclosure can be best understood when read in conjunction with the following drawings, where like structure is indicated with like reference numerals and in which:

DETAILED DESCRIPTION

Figure 1:
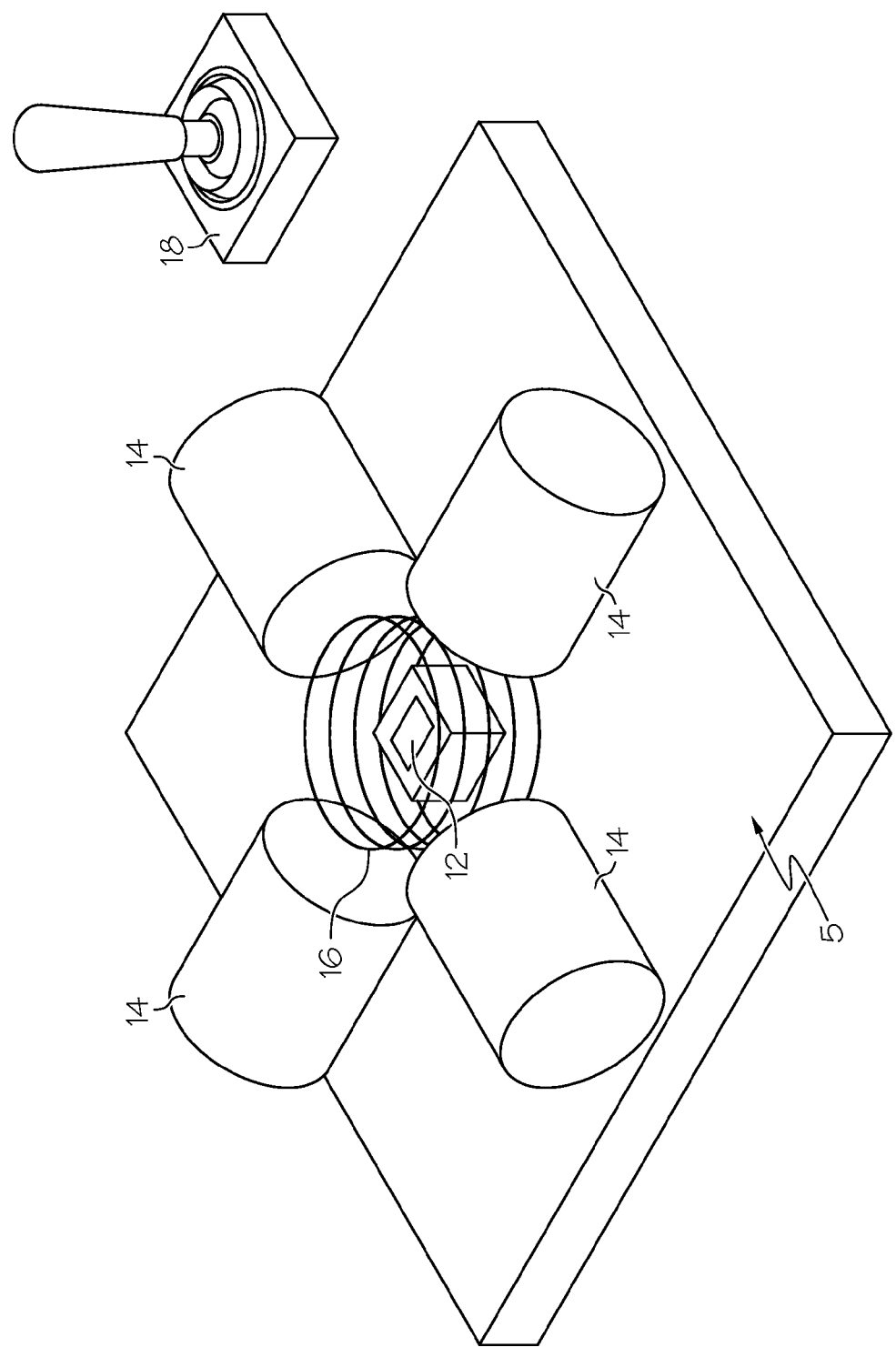
FIG. 1 shows a perspective view of a magnetic platform in accordance with one embodiment.
Figure 2:
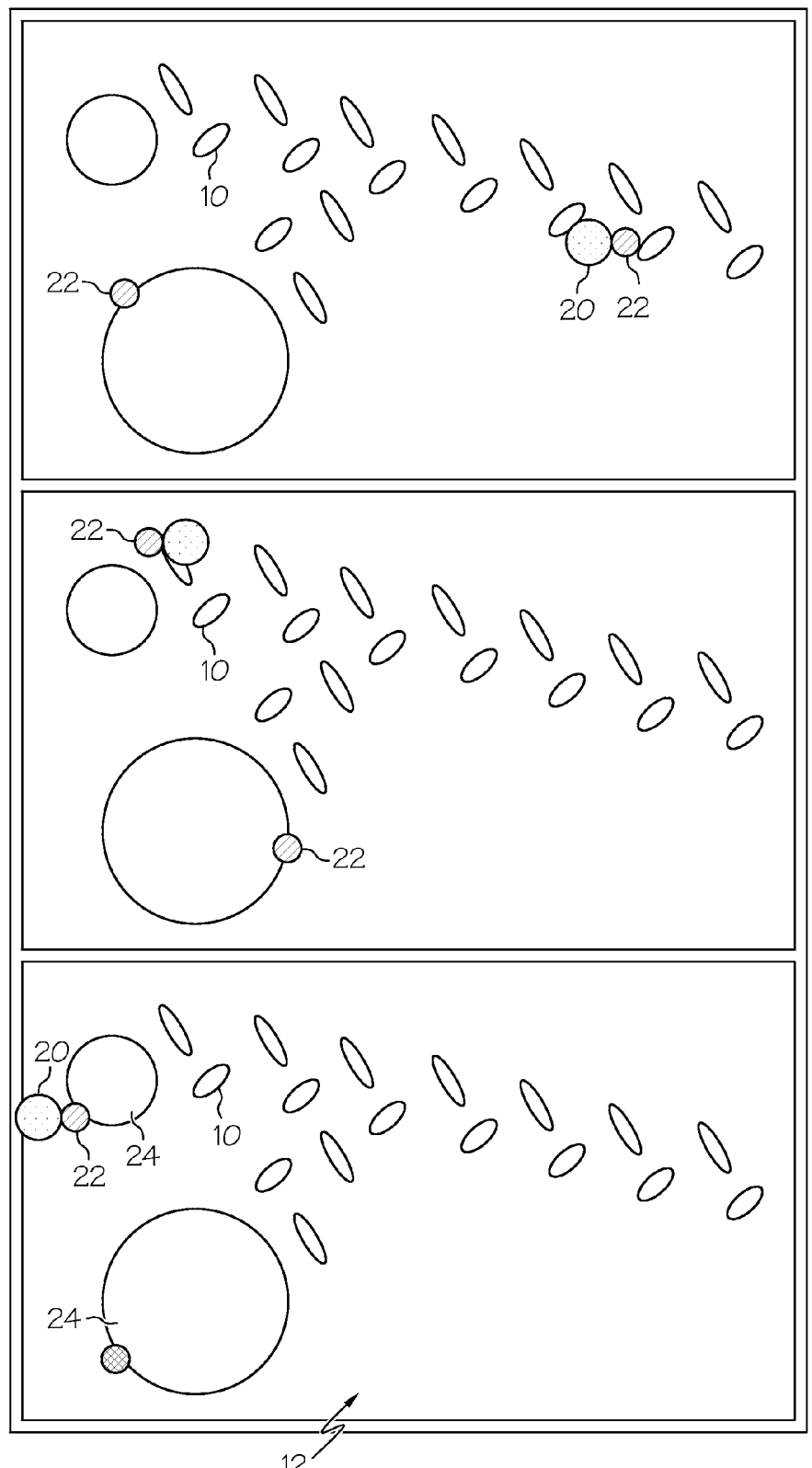
FIG. 2 is a plain view of several stages in the transport of a biomolecule on a magnetic platform as depicted in FIG. 1 in accordance with one embodiment.

Referring to FIGS. 1 and 2, a magnetic platform 5 comprises a patterned array of discrete magnetic elements positioned on a substrate 12, a plurality of first electromagnets 14 positioned adjacent to the substrate 12 for creating a first magnetic field substantially in the plane of the substrate 12, and an electromagnetic coil 16 positioned adjacent to the substrate 12 for creating a second magnetic field substantially perpendicular to the plane of the substrate 12. The magnetic platform 5 may also comprise a control device 18 for controlling the application of the first and second magnetic fields.

Magnetic fields originating from discrete micron-scale magnetic elements such as circular or elliptical disks are provided on the magnetic platform to trap and manipulate biomolecules such as cells, viruses, DNA, proteins, and other micro- or nano-scale biological material. Further details regarding the magnetic elements will be provided later in the description. As used herein, the term "biomolecule" is meant to encompass all of these micro- and macro-scale biological materials. However, it is also contemplated that the platform may be used to sort other materials and particles in addition to biomolecules.

Referring to FIG. 2, a magnetic particle 22 may be attached to a biomolecule 20 at one, or both ends of the biomolecule 20. As explained in detail below, the array of magnetic elements 10 may carry the magnetic particle 22, along with the attached biomolecule 20 towards a disk 24 for further transport and processing. Alternatively, the array of magnetic elements 10 may be arranged to transport and sort biomolecules according to a signal communicated by a control device.

Once attached, the magnetic particles 22 function as handles to transmit magnetic forces to manipulate and maneuver the biomolecules 20. The biomolecules may be attached to the magnetic particles using known chemical techniques. After attachment to the magnetic particle 22, the biomolecule 20 may be indirectly manipulated by the application of a magnetic field to cause the magnetic particle 22 to move from one magnetic element 10 to another magnetic element 10, thereby transporting the biomolecule 20 along a path defined by the array of magnetic elements 10 on the platform 5.

Because movement of a domain wall involves reorienting the magnetization vector, a domain wall traveling in narrow channels is accompanied by the emanating magnetic field that tracks along with the wall. The associated field gradients exert magnetic forces that are sufficient to trap particles as small as 5 nm, and exert forces exceeding 300 pN. Each trap therefore acts as a three-dimensional potential energy well for micro- or nano-sized objects. However, it is also contemplated that other particle sizes and forces may be utilized to capture and manipulate the particles. Domain walls and the operation of domain wall generated forces either through magnetic fields or electric currents are described in PCT Application WO 2009/143444.

The fabrication of an entire array of these magnetic elements provides an extended potential energy landscape. Such arrays and landscapes may be useful in manipulating microscopic objects, including but not limited to biomolecules, and organizing them into useful and interesting configurations. The use of continuous magnetic wires with spin polarized currents that are placed on the same platform as the array of magnetic elements provides another framework to not only study how different particles can be maneuvered along predetermined paths, but also how they move through the landscape when driven by other forces. It is also contemplated that these arrays may be useful in studying other characteristics of materials provided in these arrays.

The design, architecture, material parameters, and structural dimensions of the magnetic elements determine the specific trapping sites, domain wall profile, widths, and field gradients. Magnetic particles, with and without tethered biological entities, can be trapped at domain walls. The architecture of the magnetic elements promotes coupling of adjacent trapped particles through specific molecular links.

The magnetic elements may comprise any suitable magnetic material including, but not limited to, iron oxide, cobalt, iron, nickel and other magnetic material, and combinations thereof. In one configuration, the magnetic elements comprise FeCo. Alternatively, it is also contemplated that the magnetic elements may comprise other magnetic materials suitable to transport magnetic particles across a platform.

The magnetic particles may comprise any suitable magnetic material including, but not limited to, iron oxide, cobalt, iron, nickel and other magnetic material, and combinations thereof. In one configuration, the magnetic particles comprise FeCo.

The magnetic particles may comprise a structure selected from a group consisting of a polymer particle containing a magnetic material, a non-polymeric particle containing magnetic material, and combinations thereof. In one embodiment, the magnetic particles may be in the form of polymer particles having magnetic material embedded therein. One example of such a magnetic particle is commercially available under the trademark Dynabead. Alternatively, the magnetic particles may take other forms, such as having the magnetic material dispersed throughout the magnetic particle, or having the magnetic material make up a distinct portion of the magnetic particle. Non-polymeric particles are also contemplated where the magnetic material is surrounded by other compositions. Alternatively, the magnetic particle may also contain no coating material, and may comprise magnetic material. However, other configurations of magnetic particles are also contemplated for use in the system and methods as disclosed herein.

Generally, external magnetic fields are provided that can continuously tune the magnetic energy landscape to enable biomolecules and other objects, on a scale as small ranging from about 5 to about 10000 nanometers in size, to be maneuvered along desired trajectories. In one aspect, the associated field gradients may exert magnetic forces exceeding 100 pN. However, other field gradients are also contemplated.

Referring again to FIG. 1, in one embodiment, the external in-plane first magnetic field may be created by four orthogonally spaced electromagnets 14. Alternatively, the external in-plane magnetic field may be produced with other arrangements and orientations of magnets. A perpendicular second magnetic field may be produced by an electromagnetic coil 16. However, the perpendicular magnetic field may also be provided in other fashions. The electromagnets and electromagnetic coil may be of any type suitable to create a magnetic field operable to transport a biomolecule on the platform.

Figure 3:
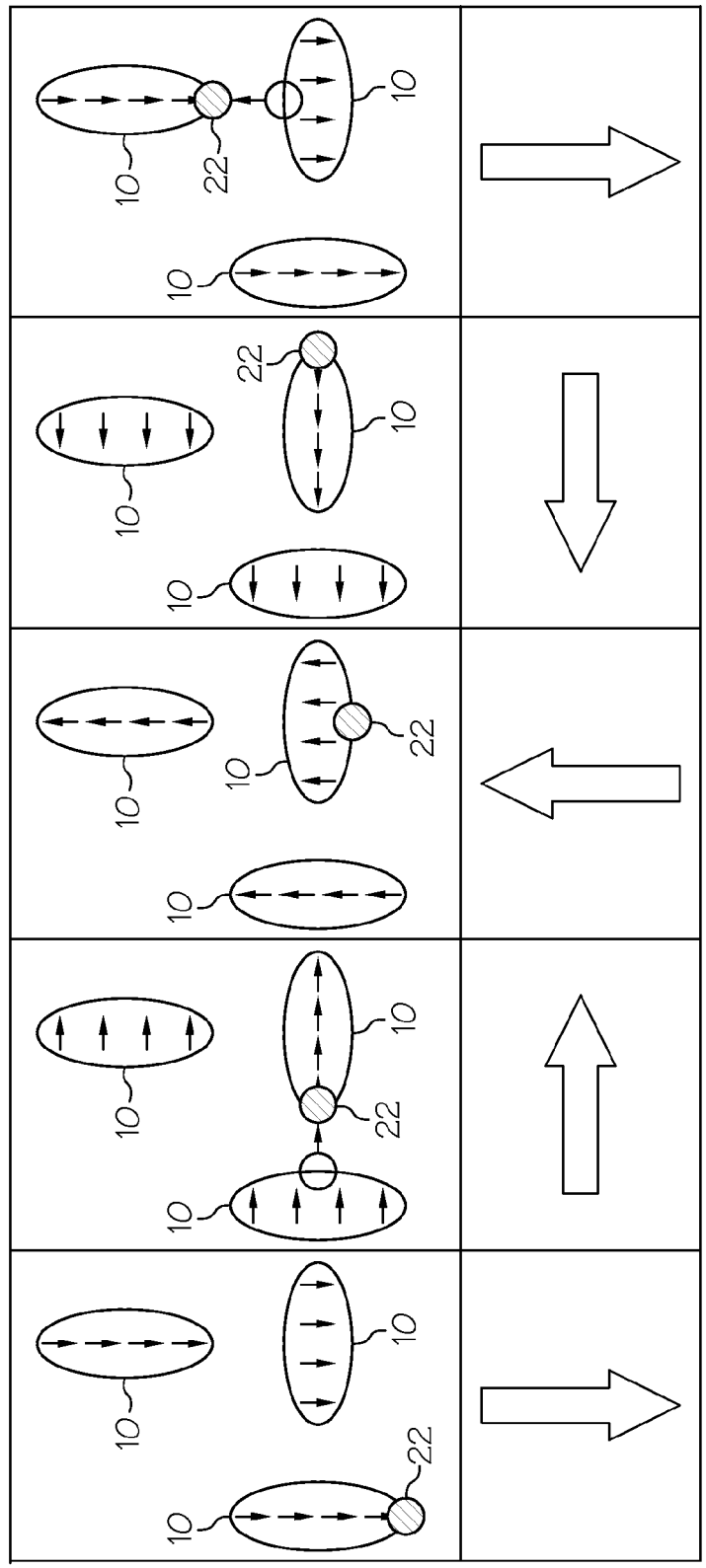
FIG. 3 schematically illustrates the use of in-plane and perpendicular magnetic fields to move a magnetic particle on the magnetic platform depicted in FIG. 1 in accordance with another embodiment.

Referring to FIG. 3, by remotely switching the direction of the perpendicular second field between out-of-plane and into-plane orientations, as well as rotating the in-plane first magnetic field, the magnetic particles 22 can be moved to a specific location on the planar array. The orientation of the in-plane magnetic field is shown by arrows, while the perpendicular fields are represented by circle with enclosed dot (out-of-plane) or cross (into-plane). Furthermore, it is also contemplated that other magnetic field arrangements may be useful in conjunction with the systems and methods disclosed herein.

In one configuration, the first magnetic field may have a strength ranging from about 1 to about 500 Gauss, and the second magnetic field may have a strength ranging from about 1 to about 500 Gauss. The fields may also have other strengths suitable to enable the platform to sort, manipulate, and trap particles as described herein.

The magnetic elements may be provided in a variety of sizes suitable to provide the sorting and trapping functionality described herein. In one embodiment, the magnetic elements may have a length ranging from about 100 to about 10000 nanometers, and a height ranging from about 10 to about 500 nanometers. The magnetic elements may also have a length ranging from about 100 to about 1000 nanometers, and height ranging from about 20 to about 200 nanometers. However, other lengths and widths of the magnetic elements are also contemplated for use with the magnetic platform disclosed herein.

The magnetic elements may have a shape selected from the group consisting of circular disks, elliptical disks, oval disks, and wires. Alternatively, it is also contemplated that the magnetic elements may take other forms and shapes suitable to transport and orient biomolecules on a magnetic platform. In one configuration, the magnetic elements may be elliptically shaped disks having an aspect ratio of about 3:1. However, other aspect ratios and shapes are also contemplated. Depending on the shape of the magnetic elements, their magnetization will align such that they act like tiny bar magnets or develop regions of different magnetizations that are separated by magnetic domain walls. By manipulating the external magnetic fields, the configuration of the array and shapes of the magnetic elements, biomolecules can be trapped and transported to a desired location.

Figure 4:
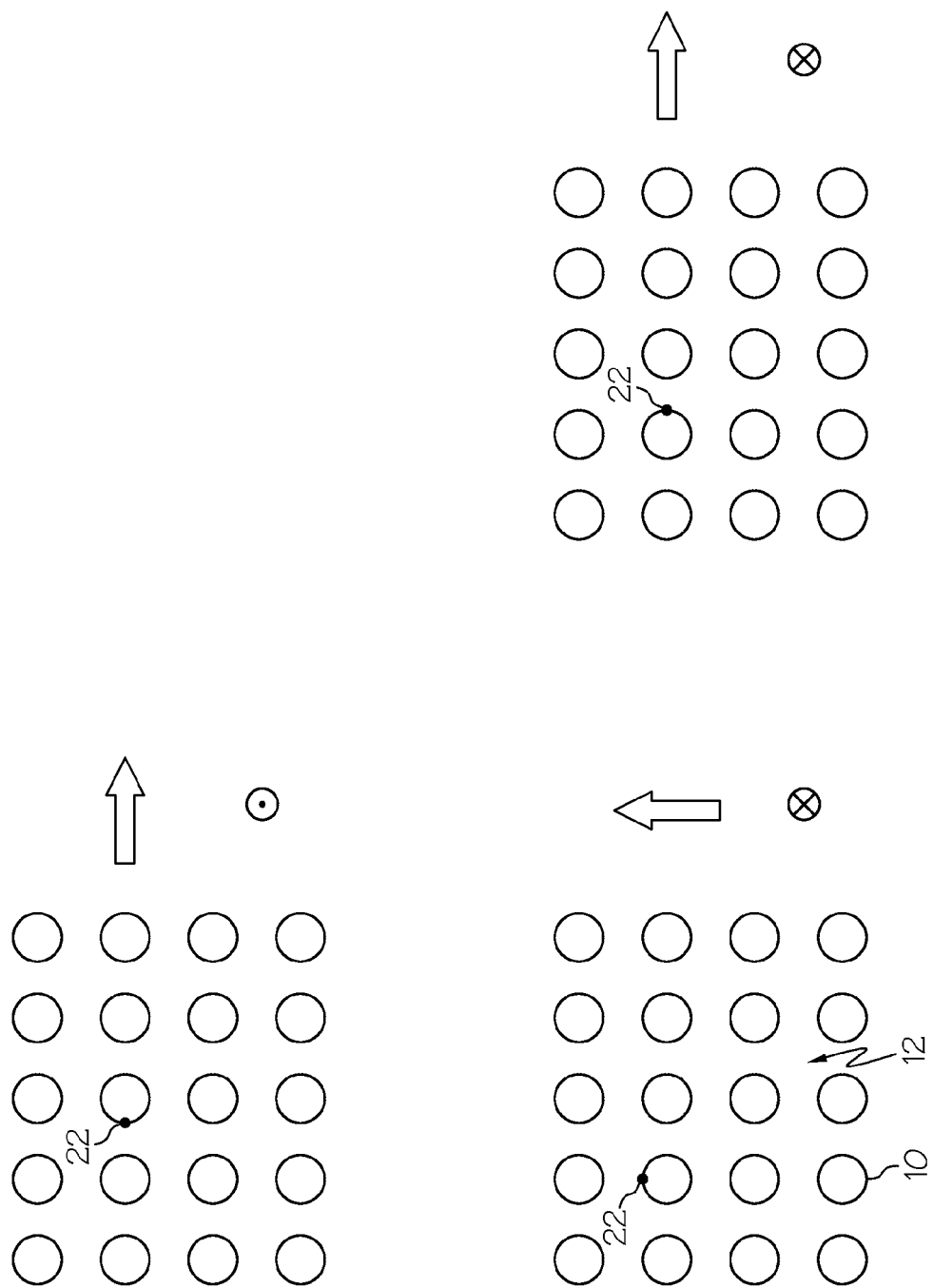
FIG. 4 schematically illustrates the changing magnetic fields of the magnetic platform as depicted in FIG. 1 in accordance with one embodiment.

Referring to FIG. 4, in addition to ellipses, the magnetic elements 10 may have a circular shape. The circularly shaped elements 10 may trap magnetic particles 22, and then transport them around their edge by rotating the magnetic field. At desired locations on the circumference of the magnetic element, the magnetic particles 22 with attached biomolecule can be induced to jump to the next magnetic element 10 by manipulating the magnetic fields.

Referring again to FIG. 2, by "patterned array," we mean an interconnected system of at least two such magnetic elements 10 positioned adjacent to one another. An example would be an array of elliptical disks such that the spacing between the adjacent disks in the array varies. Using lithography techniques, arrays of magnetic elements 10 are created with nanoscale precision that enable well-defined planar assemblies of micron- or nano-scale magnetic elements 10 to be created such that biomolecules 20 attached to magnetic particles 22 may be trapped and manipulated on and along the surface of such arrays. In one embodiment, the long axis of each magnetic element is oriented at a right angle to the adjacent magnetic element's long axis. Alternatively, the magnetic elements 10 may be oriented in other ways, such as at a substantially right angles to one another, or even in an orientation roughly 45° in respect to the adjacent magnetic element 10. It is also contemplated that the patterned array of magnetic elements may be arranged in other patterns suitable to sort and transport biomolecules and other particles across the platform 5.

The distance between the magnetic elements in the patterned array may vary depending on the size of the biomolecules, the strength of the magnetic fields, and many other factors. In one configuration, the distance between the magnetic elements ranges from about 100 to about 10000 nanometers. However, it is also contemplated that the distance between the magnetic elements may be any distance suitable to provide transport to the biomolecules across the substrate.

As will be understood, the design and architecture of the patterned arrays enable different trapping site configurations to be fabricated. This permits the fabrication of two-dimensional magnetic platforms having different layouts for trapping micro- and nano-sized magnetic particles at specific locations. Such magnetic platforms enable the study of individual molecules, the interactions between large molecules, and the response of such molecules to external stimuli.

Referring to FIG. 2, the magnetic elements 10 may be provided on the substrate 12 using photolithography techniques that involve coating a substrate 12 with a layer of electron beam resistive material, writing the desired pattern using electron beam lithography, and sputtering a thin film of magnetic material onto a substrate 12. The lithography, in conjunction with known developing processes, can also remove the resistive material thus enabling the magnetic elements 10 to be sputtered on to the substrate 12 to create the desired pattern or array. The patterns may be chosen based on results from a simulation program which models the magnetic domains in thin films in the presence of external magnetic fields. The substrate may comprise silicon, silica oxide-based glass, metal oxide, polymer, or combinations thereof. The film may have a thickness ranging from about 10 to about 1000 nm. The lithographic creation of the arrays allows the architecture of the magnetic platform to be designed and fabricated with spatial resolutions determined by present nano-scale fabrication techniques. One example of a suitable simulation program is provided by Donahue, M. J., and D. G. Porter. See 1999 OOMMF User's Guide, Version 1.0, Interagency Report NISTIR 6376, National Institute of Standards and Technology, Gaithersburg, Md. This public code can be found at the URL http://math.nist.gov/oommf/.

Referring again to FIG. 1, a control device 18 may be provided for controlling the application of the first and second magnetic fields. In one embodiment, the control device 18 comprises a voltage controller and a current controller, electrically connected to the plurality of first electromagnets 14 and the electromagnetic coil 16. The voltage controller may regulate the voltage transmitted to the magnets and coil to ensure that the desired voltage is provided to each of the magnets and coil. In addition, the current controller may regulate the amount of current supplied to the electromagnets and coil to ensure the desired transport and movement on the platform 5. The control device 18 may be a joystick, where manipulation of the joystick corresponds to movement of the magnetic particles, achieved through programming of a software application. Alternatively, the control device 18 may be a range of other devices suitable to direct the magnetic fields on the platform 5 to effect the transport and sorting of a biomolecule, such as voice-activated controls. The control device may be programmed using software such as LabView, or other software systems.

In one embodiment, digital signals from the joystick are transmitted to the digital inputs on a data acquisition card of a computer. The signals from the data acquisition card may be read by LabVIEW routines which then interpret what magnetic field should be transmitted based on the signals from the control device to effect the desired movement or sorting. The signals may operate at a range of voltages, ranging from about 0 to about 5 volts. However, other voltages are also contemplated for use. A LabVIEW routine may also calculate the necessary voltage required to control the movement of the particle based on input from the control device. The voltage signals may be amplified before driving current through the electromagnets and the coil. Alternatively, other systems may be used to control the interaction between the control device and the current and voltage supplied to the plurality of electromagnets and coils.

The in-plane electromagnets may be operated at a voltage range from about 0 to about 20 volts. The current supplied to the in-plane electromagnets may range from about 0 to about 500 mA. The power supplied to the in-plane electromagnets ranges from about 0 to about 10 Watts. However, other power and current ranges are also contemplated for use with the methods disclosed herein.

The out-of-plane electromagnets may be operated at a range of voltages ranging from about 0 to about 3.6 volts. The current supplied to the out-of-plane electromagnets may range from about 0 to about 5 A. The power supplied to the out-of-plane electromagnets ranges from about 0 to about 18 Watts. However, other power and current ranges are also contemplated for use with the methods disclosed herein.

Referring to FIG. 4, in one embodiment, magnetic particles 22 are attracted to the magnetic elements 10 through the magnetic field associated with each magnetic element 10. In response to the rotating in-plane magnetic field, the magnetization of each magnetic element 10 changes the orientation of the field, causing the magnetic particle 22 with biomolecule attached to become trapped and transported along the circumference of the magnetic element 10. Upon reaching the vicinity of a neighboring magnetic element 10, the magnetic particles 22 "jump" from one magnetic element 10 to the neighboring magnetic element 10. The direction of rotation of the external magnetic field may be reversed to change the direction of magnetic particle 22 movement. Eventually, as shown in FIG. 2, a magnetic particle 22 may be loaded onto a desired circular disk 24 that is at the end of the patterned array for further transport and processing. The magnetic particles 22 may be attached to a biomolecule in a variety of manners, including attaching at the end of the biomolecule, attaching at a median point on the biomolecule, and at other portions of the biomolecule as well.

Figure 5:
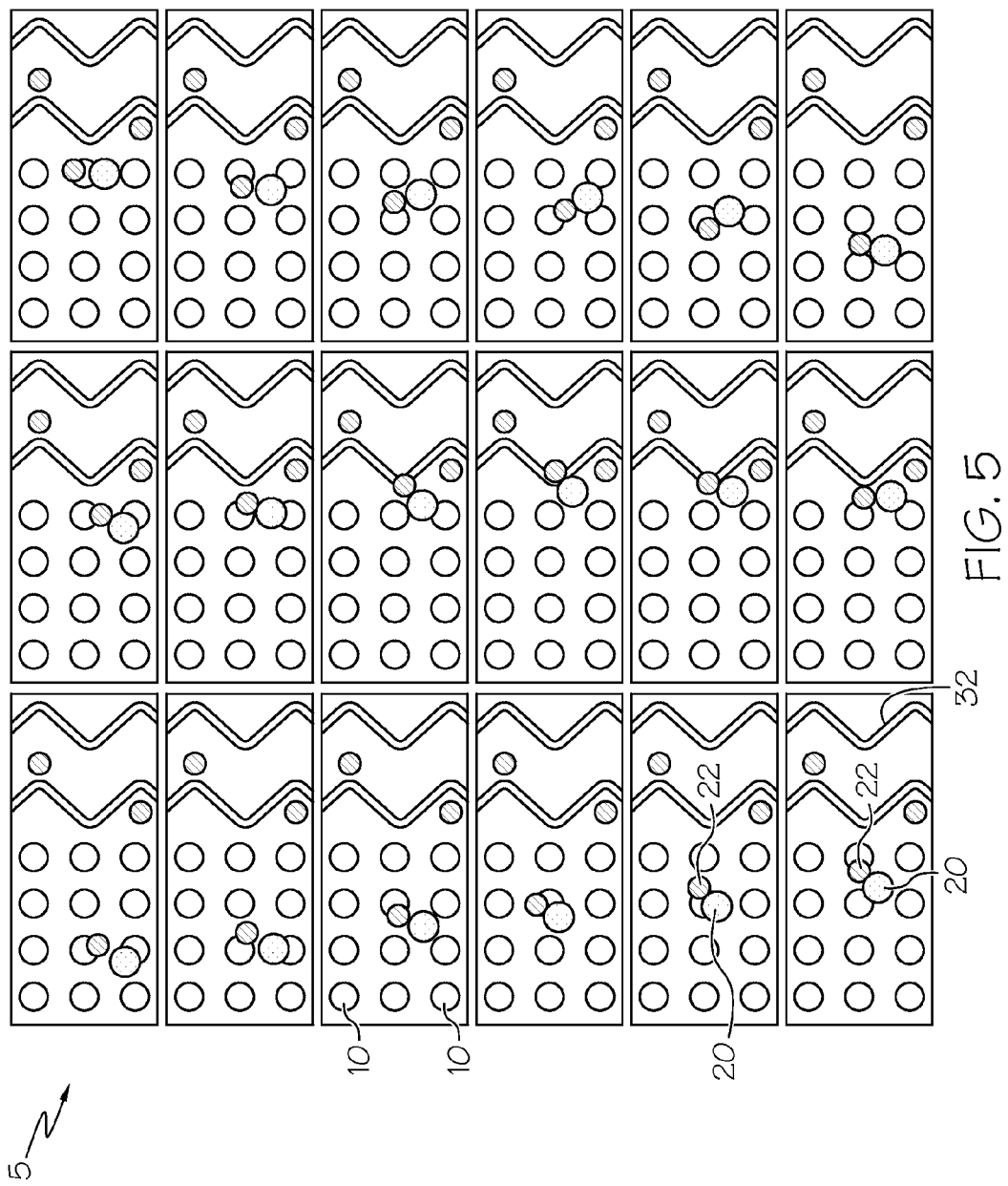
FIG. 5 schematically illustrates the transport of a biomolecule in conjunction with the magnetic platform of FIG. 1 in accordance with another embodiment.

Referring to FIG. 5, in one example, a biomolecule 20 may be a single human T-lymphocyte cell. The cell may be attached to a magnetic particle 22. In this example, the magnetic elements were 5 μm diameter disks spaced apart at 5 μm intervals. Previously separated T cells (CD3 positive) from human blood cells were attached to magnetic particles 22 using known chemical techniques. The magnetic particles 22 and attached biomolecules 20 were transported across the platform 5 via the magnetic elements 10. The molecules were then transported to the continuous wire on which it could be maneuvered by a magnetic field or electric current.

Figure 6:
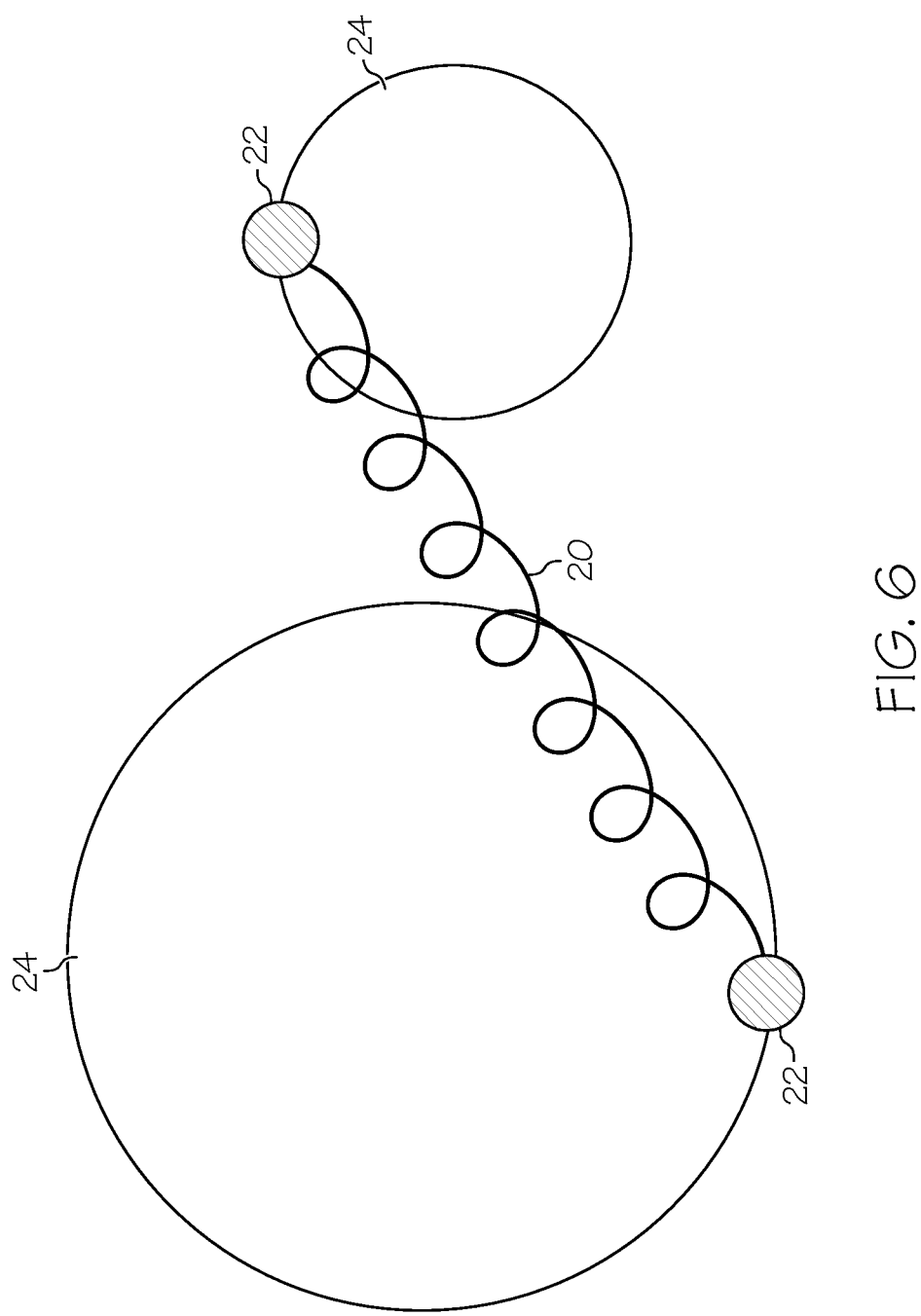
FIG. 6 illustrates a process of manipulating a biomolecule in conjunction with the magnetic platform depicted in FIG. 1 in accordance with yet another embodiment.

Referring to FIG. 6, in another embodiment, the magnetic platform may be used as a device resembling a pair of magnetic tweezers. In one configuration, two circular disks 24 of different diameters may be provided on the platform 5 adjacent to one another. Magnetic particles 22 may be attached to opposite sides of a biomolecule 20 in the manner described above. The loaded magnetic particles 22 may be attached to the disks 24 through magnetic attraction. The biomolecule 20 may be stretched by rotating the disks 24 in opposite directions by applying the magnetic fields. The trapped biomolecule 20 may then be transformed back to its original shape by reversing the current flow, thereby compressing the biomolecule 20. More generally, the magnetic particles 22 may act as handles for the biomolecule 20, allowing the object to be compressed, twisted, and manipulated in other ways. It is also contemplated that the magnetic particles may be attached to other objects to provide a platform for manipulation of the objects. The magnetic platform configuration described permits real-time observations of single or multiple molecules or other small objects trapped and controllably manipulated in a two-dimensional environment.

Figure 7:
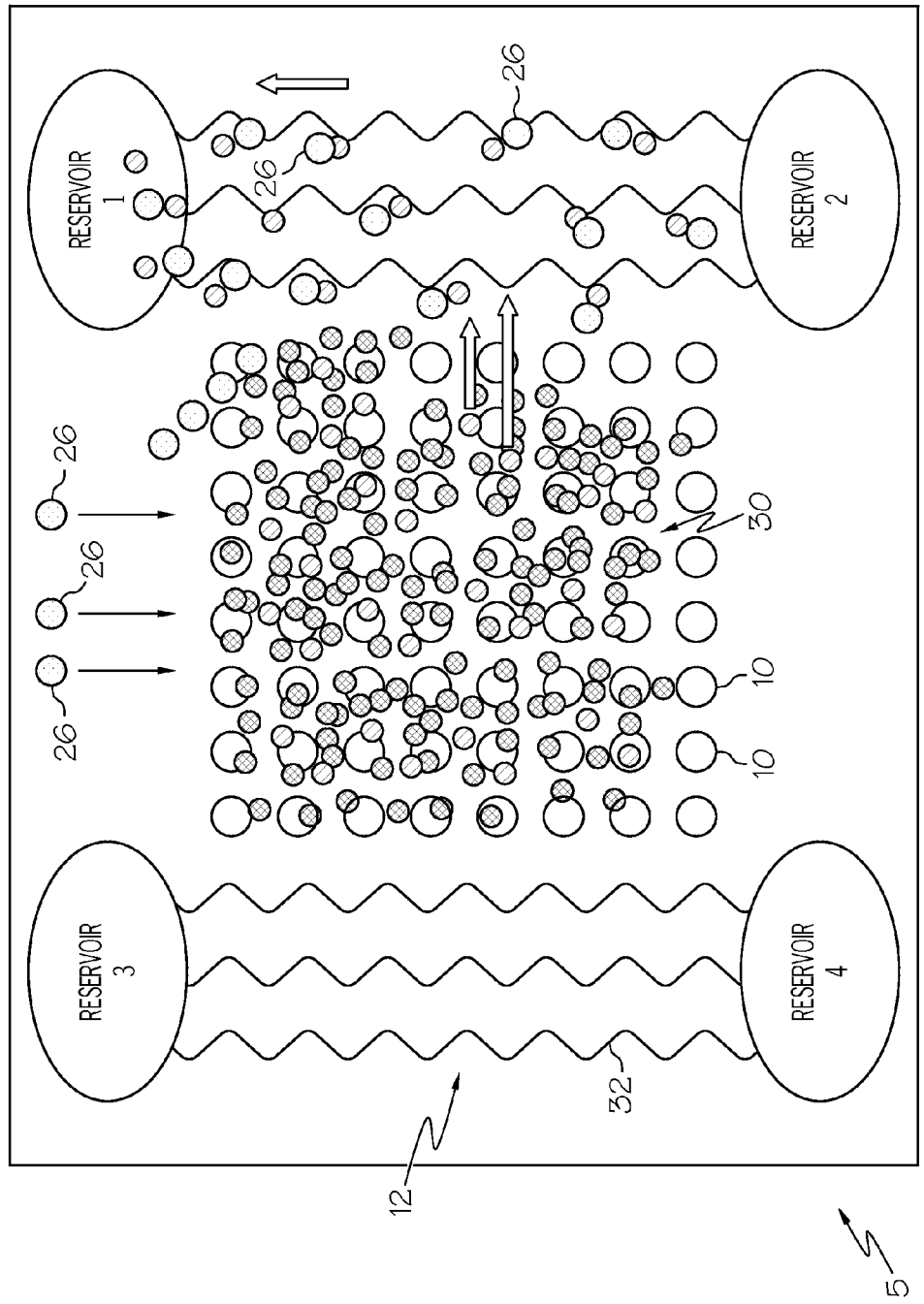
FIG. 7 illustrates a suspension disposed on the magnetic platform depicted in FIG. 1 in accordance with one embodiment.

Referring to FIG. 7, in yet another embodiment, the magnetic platform 5 allows magnetically labeled cells to be separated and sorted from unlabeled cells. In one configuration, a suspension 30 of a cell mixture may be provided on the magnetic platform 5. The suspension 30 may comprise a wide range of compositions and consistencies, containing numerous cell types. An appropriate amount of first anti-body magnetic particle conjugates 26 may be introduced to the suspension 30 of cells that target a first cell type of interest. These conjugates may selectively bond to the first cell type by known bonding techniques in order to provide a magnetic component to the target cells. The magnetic elements 10 may be activated using magnetic fields to transport the magnetically labeled particles to one side of the magnetic platform 5, and a plurality the zigzag shaped wires 32 in the manner described above. The wires 32 may then be magnetically activated to transport the cells along the wires 32 and away from the suspension 30 for further transport and processing.

Once all of the first antibody-magnetic particle conjugates 26 are removed, a second anti-body magnetic particle conjugate (not shown) may be provided targeting the next cell type of interest. The process may be repeated as many times as desired to separate cell types of interest from the cell suspension 30.

Figure 8:
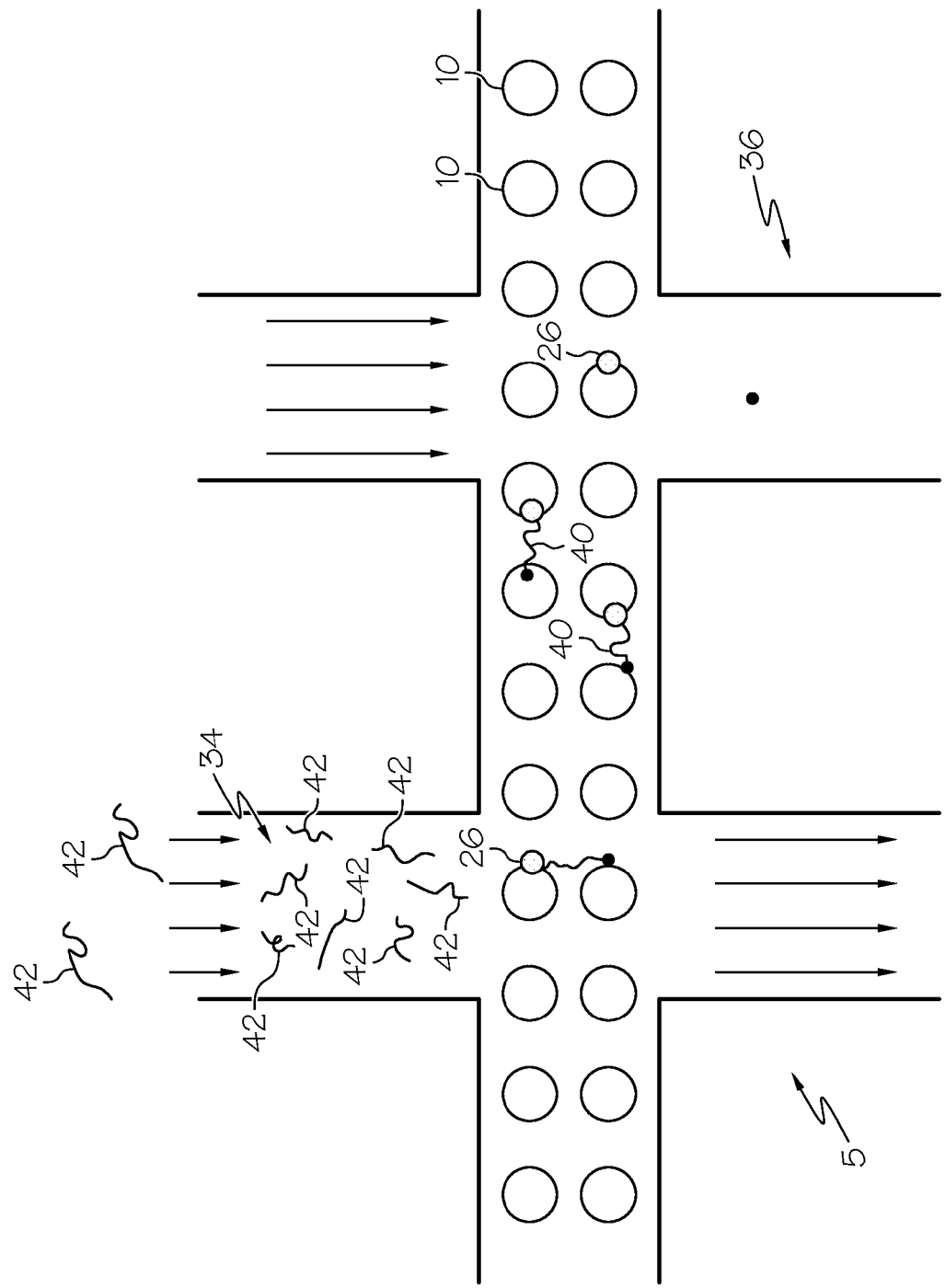
FIG. 8 is a plain view of a magnetic platform in conjunction with a micro fluidic device in accordance with another embodiment.

Referring to FIG. 8, in another embodiment, the magnetic platform 5 may be used in conjunction with a micro fluidic device. The micro fluidic device may comprise an array of discrete magnetic elements 10. In one aspect, a mixture of magnetically labeled biomolecules 40 and unlabeled biomolecules 42 are flowed through a first fluid channel 34. Alternatively, any number of biomolecule types may be provided in the first fluid channel. The magnetically labeled biomolecules 40 are attached to the magnetic particles 22 and are trapped on magnetic elements 10.

The magnetic fields produced by the magnetic platform may be selectively controlled by a control device to cause the magnetically labeled biomolecules to be transported from the first fluid channel 34 to the second fluid channel 36 along the array of magnetic elements 10. In one configuration, selectively controlling the magnetic field may include switching the direction of the second magnetic field between out of plane and in-plane orientations, and rotating the first magnetic field. However, it is also contemplated that there are other means of selectively controlling the magnetic fields that may be used in order to transport a magnetic particle 22 or a biomolecule 20 across a micro fluidic device.

After relocation to the second fluid channel 36, the magnetically labeled biomolecules 40 are detached from the magnetic elements 10 on the platform 5 in the second fluid channel 36 by for example, chemical means, such as use of suitable enzymes. It is contemplated that the process may be repeated in multiple iterations in order to sort a mixture of biomolecules 20 comprising more than two biomolecule types, by magnetically labeling one group of biomolecules 20 and sorting them into a fluid channel, and then labeling an additional group of biomolecules 20, and sorting them into an additional fluid channel, until all types of biomolecules 20 are sorted as desired. Although two fluid channels are shown, it is understood that a plurality of fluid channels may be used to suit the requirements of the sorting process, and sort larger or more diverse groups of biomolecules.

The availability of mobile magnetic traps as described herein offers new control that is needed for rapid progress in several branches of science and engineering. In particular, the femto- to pico-Newton scale forces linked to the methods and devices described herein are ideally suited for probing single microparticles and biomolecules 20 ranging from the about 10 to about 10000 nm length scales. In physics and chemistry, the methods and devices described herein can provide an understanding of nanoclusters in the transition region between single molecule and microscopic structures where puzzling challenges remain. In biology, the methods and devices described herein can be used to study many vital inter- and intra-cellular processes. Nanoscale engineering will benefit from the options provided by the described methods and devices for organizing, manipulating, and analyzing individual tiny objects. The tunable magnetic trap arrays and methods of use as described herein meet these needs.

Industrial applications which rely on transporting magnetic nanoparticles cover a broad spectrum. The methods and devices described herein have utility in micro fluidic devices to manipulate fluid-borne entities inside a network of microscopic channels for clinical diagnosis, forensic applications, and environmental analysis. Specifically, the mobile magnetic traps, used in conjunction with micro fluidics channels can be used to separate cells and/or particles of interest from a variety of fluids including blood, plasma, or other body fluids as well as water or other fluid samples. Embodiments of the present invention may also find use in portable devices for environmental and medical analysis.

It is also noted that recitations herein of "at least one" component, element, etc., should not be used to create an inference that the alternative use of the articles "a" or "an" should be limited to a single component, element, etc.

It is noted that recitations herein of a component of the present disclosure being "programmed" in a particular way, "configured" or "programmed" to embody a particular property, or function in a particular manner, are structural recitations, as opposed to recitations of intended use. More specifically, the references herein to the manner in which a component is "programmed" or "configured" denotes an existing physical condition of the component and, as such, is to be taken as a definite recitation of the structural characteristics of the component.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A process for manipulating one or more biomolecules in substantially a single plane comprising:
   providing a magnetic platform comprising a patterned array of discrete magnetic elements positioned on a substrate, a plurality of first electromagnets positioned adjacent to the substrate for creating a first magnetic field substantially in the plane of said substrate, an electromagnetic coil positioned adjacent to the substrate for creating a second magnetic field substantially perpendicular to the plane of said substrate, and a control device for controlling the application of said first and second magnetic fields to said magnetic elements to change the orientation of the magnetic field in said magnetic elements;
   providing one or more biomolecules adjacent said patterned array;
   trapping said one or more biomolecules on said patterned array; and
   manipulating said one or more biomolecules by controlling said first magnetic field in the plane of said patterned array.

2. The process of claim 1 wherein said one or more biomolecules have magnetic particles attached thereto.

3. The process of claim 2 in which manipulating said one or more biomolecules causes said one or more biomolecules to compress or stretch.

4. The process of claim 2 wherein the magnetic particles comprise a structure selected from a group consisting of a polymer particle containing a magnetic material, a non-polymeric particle containing magnetic material, and combinations thereof.

5. The process of claim 2, wherein the magnetic particles have a diameter ranging from about 10 to about 10000 nm.

6. The process of claim 2, further wherein manipulating said one or more biomolecules further comprises providing two disks; attaching said magnetic particles to opposite ends of the one or more biomolecules; attaching said magnetic particles to each of said disks; and manipulating the one or more biomolecules by rotating said disks in opposite directions.

7. The process of claim 2 in which manipulating said one or more biomolecules causes said one or more biomolecules to move from one element to another in said patterned array.

8. The process of claim 1 wherein said one or more biomolecules comprise a suspension of mixed biomolecules; and wherein manipulating said one or more biomolecules comprises adding antibody-magnetic particle conjugates for a first biomolecule type to said suspension to couple with said first biomolecule type; and selectively controlling the magnetic fields produced by said platform to cause said coupled first biomolecule type to be sorted from said cell suspension.

9. The process of claim 8 wherein selectively controlling the magnetic field comprises switching the direction of the second magnetic field between out of plane and in-plane orientations, and rotating the first magnetic field.

10. The process of claim 1 wherein said one or more biomolecules comprise a mixture of magnetically labeled and unlabeled biomolecules and manipulating said one or more biomolecules comprises flowing said mixture through a first fluid channel; trapping said magnetically labeled biomolecules on said magnetic platform; selectively controlling the magnetic fields produced by said platform to cause said magnetically labeled biomolecules to be transported from said first fluid channel to a second fluid channel; and detaching said magnetically labeled biomolecules from said platform in said second fluid channel.

11. The process of claim 10 wherein the control device comprises a joystick.

12. The process of claim 11 wherein selectively controlling the magnetic field comprises switching the direction of the second magnetic field between out of plane and in-plane orientations, and rotating the first magnetic field.

* * * * *